United States Patent
Takahashi

(10) Patent No.: US 11,341,666 B2
(45) Date of Patent: May 24, 2022

(54) IMAGE PROCESSING DEVICE, ENDOSCOPE SYSTEM, OPERATION METHOD OF IMAGE PROCESSING DEVICE, AND COMPUTER-READABLE RECORDING MEDIUM

(71) Applicant: OLYMPUS CORPORATION, Tokyo (JP)

(72) Inventor: Jumpei Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 461 days.

(21) Appl. No.: 16/662,179

(22) Filed: Oct. 24, 2019

(65) Prior Publication Data
US 2020/0058131 A1    Feb. 20, 2020

Related U.S. Application Data

(63) Continuation of application No. PCT/JP2017/016628, filed on Apr. 26, 2017.

(51) Int. Cl.
*G06K 9/00*      (2022.01)
*G06T 7/586*    (2017.01)
(Continued)

(52) U.S. Cl.
CPC ............ *G06T 7/586* (2017.01); *A61B 1/0005* (2013.01); *A61B 1/0638* (2013.01);
(Continued)

(58) Field of Classification Search
CPC .............. A61B 1/00009; A61B 1/0002; A61B 1/00045; A61B 1/0005; A61B 1/045;
(Continued)

(56) References Cited

U.S. PATENT DOCUMENTS

2011/0263940 A1* 10/2011 Yamaguchi .......... A61B 1/0638
                                                                          600/163
2015/0363932 A1* 12/2015 Hirota .............. A61B 1/000094
                                                                          382/128
(Continued)

FOREIGN PATENT DOCUMENTS

| JP | 5393525 B2 | 1/2014 |
| JP | 2016-093210 A | 5/2016 |
| JP | 2016-144626 A | 8/2016 |

OTHER PUBLICATIONS

International Search Report dated Jul. 18, 2017 issued in PCT/JP2017/016628.
English Abstract of JP 2011-167349 A dated Sep. 1, 2011.

*Primary Examiner* — Avinash Yentrapati
(74) *Attorney, Agent, or Firm* — Scully, Scott, Murphy & Presser, P.C.

(57) ABSTRACT

An image processing device includes: an image acquiring unit configured to acquire a plurality of images that are captured with a same angle of view and are different from each other in a wavelength band of illumination light; a processor including hardware. The processor is configured to determine, based on a first image and a second image different from the first image in the plurality of images, whether a first light absorber in a living body in the first image and a second light absorber in a living body in the second image overlap in a depth direction of a living body, and extract light-absorption information as a result of absorption by the first light absorber, by using the first image, the second image, and a determination result.

17 Claims, 8 Drawing Sheets

(51) Int. Cl.
*A61B 1/00* (2006.01)
*A61B 1/06* (2006.01)

(52) U.S. Cl.
CPC .............. *G06T 2207/10068* (2013.01); *G06T 2207/10152* (2013.01); *G06T 2207/30004* (2013.01)

(58) Field of Classification Search
CPC ... A61B 1/0638; A61B 1/0646; A61B 1/0684; A61B 1/0661; A61B 1/0669; A61B 1/0676; G06T 2207/10068; G06T 2207/10152; G06T 2207/30004; G06T 7/586
See application file for complete search history.

(56) References Cited

U.S. PATENT DOCUMENTS

| | | | |
|---|---|---|---|
| 2017/0209031 A1* | 7/2017 | Nakamura | A61B 1/00045 |
| 2017/0258296 A1* | 9/2017 | Kaku | A61B 1/04 |
| 2019/0005641 A1* | 1/2019 | Yamamoto | G06T 7/0012 |

* cited by examiner

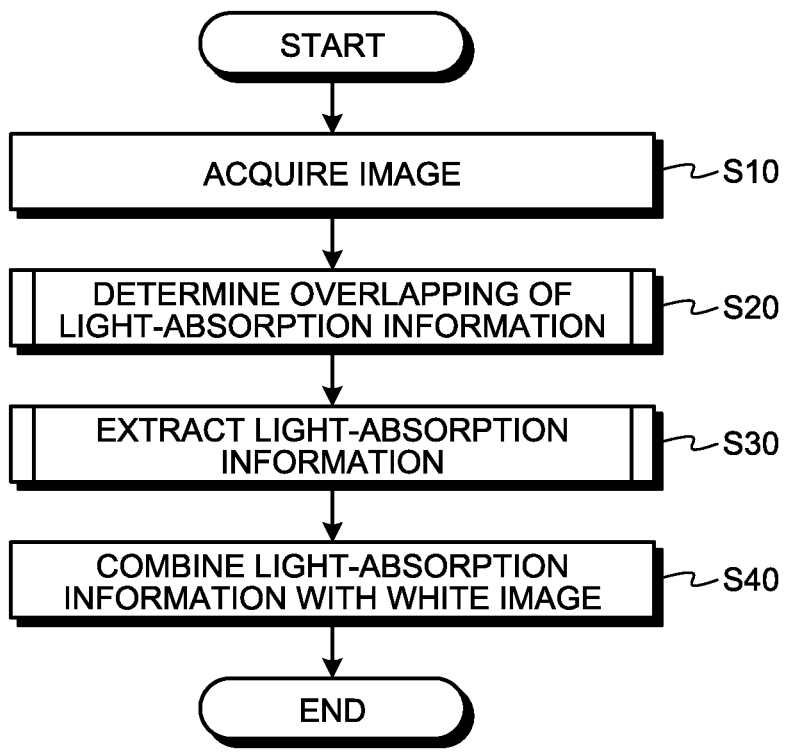

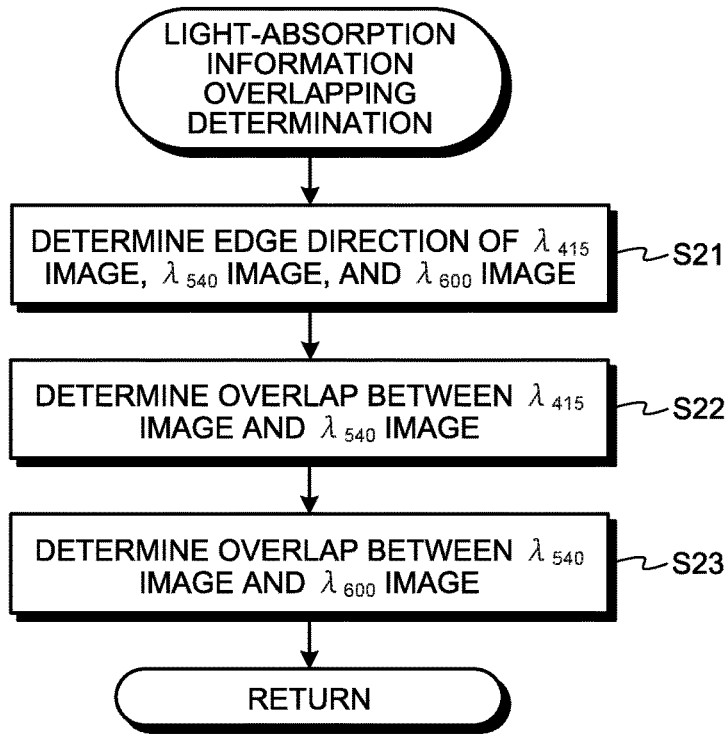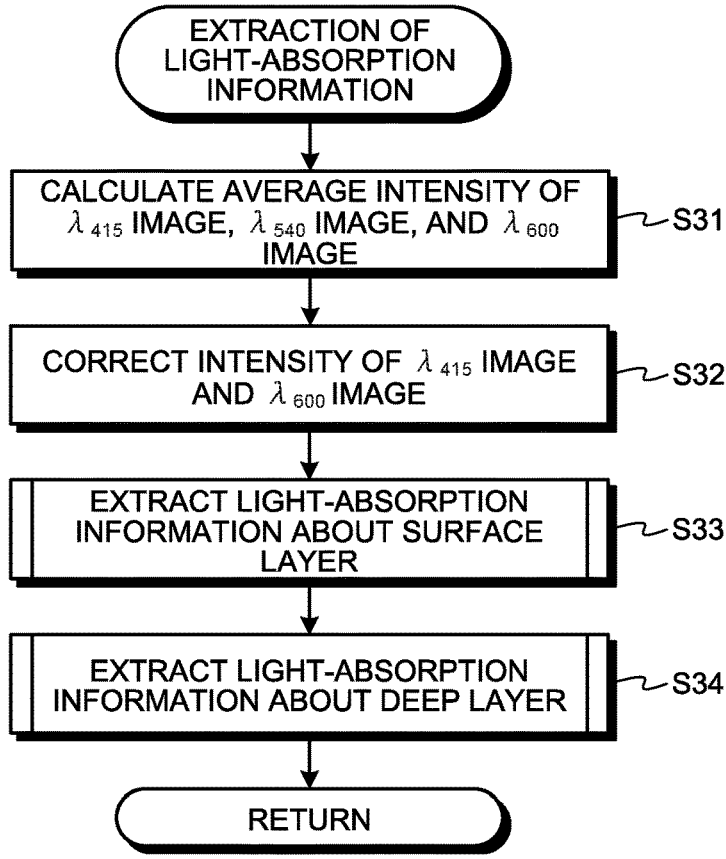

(a)  (b)

(a)  (b)

(a)                               (b)

IMAGE PROCESSING DEVICE, ENDOSCOPE SYSTEM, OPERATION METHOD OF IMAGE PROCESSING DEVICE, AND COMPUTER-READABLE RECORDING MEDIUM

CROSS-REFERENCE TO RELATED APPLICATION

This application is a continuation of International Application No. PCT/JP2017/016628, filed on Apr. 26, 2017, the entire contents of which are incorporated herein by reference.

BACKGROUND

1. Technical Field

The present disclosure relates to, for example, an image processing device that performs image processing on an image captured by an endoscope, an endoscope system, an operation method of the image processing device, and a computer-readable recording medium.

2. Related Art

In the related art, endoscope apparatuses have been widely used for various inspections in the medical field and the industrial field. Among these, medical endoscope apparatuses feature insertion of a flexible insertion portion, having a thin and long shape and having a distal end provided with an image sensor with a plurality of pixels, into a subject such as a patient. Thus, an in-vivo image of the subject can be acquired without cutting the subject, meaning that a damage to the subject is small. With such a feature, the medical endoscopes are popularly used.

In diagnosis using a medical endoscope apparatus, observation is made on blood vessels, at a specific depth from a mucosal surface which depends on a purpose of the diagnosis. For example, cancer in the digestive tract often develops in a range between a surface layer and a deep layer of a mucosa. Therefore, in early cancer screening, it is important to observe an image of blood vessels in the surface layer of the mucosa. On the other hand, when ablating a lesion, in order to suppress bleeding at the time of ablation, an image of a thick blood vessel (artery) in the deep layer of the mucosa is observed.

JP 5393525 B2 discloses a method of extracting a blood vessel at a specific depth based on the correlation between the wavelengths of colors in an endoscopic image using three bands of red (R), green (G) and blue (B). For example, since blue light with a short wavelength is reflected on the surface layer of the mucosa, blood vessels on the surface layer of the mucosa are visualized in an image based on the blue light. On the other hand, since green light more on a longer wavelength side than blue is reflected on a layer deeper than that corresponding to blue light, blood vessels in a middle layer of the mucosa are visualized in an image based on this green light. Based on such light reflection characteristics, it is possible to visualize blood vessels at a specific depth by using the correlation between the images based on the colors.

SUMMARY

In some embodiments, an image processing device includes: an image acquiring unit configured to acquire a plurality of images that are captured with a same angle of view and are different from each other in a wavelength band of illumination light; a processor including hardware. The processor is configured to determine, based on a first image and a second image different from the first image in the plurality of images, whether a first light absorber in a living body in the first image and a second light absorber in a living body in the second image overlap in a depth direction of a living body, and extract light-absorption information as a result of absorption by the first light absorber, by using the first image, the second image, and a determination result.

In some embodiments, an endoscope system includes: an endoscope configured to generate image data by imaging an inside of a body of a subject when being inserted into the subject; and the image processing device configured to execute image processing with respect to an endoscopic image corresponding to the image data generated by the endoscope.

In some embodiments, provided is an operation method of an image processing device. The operation method includes: acquiring a plurality of images that are captured with a same angle of view and are different from each other in a wavelength band of illumination light; determining, based on a first image and a second image different from the first image in the plurality of images, whether a first light absorber in a living body in the first image and a second light absorber in a living body in the second image overlap in a depth direction of a living body in the images; and extracting light-absorption information as a result of absorption by the first light absorber, by using the first image and the second image and a determination result obtained by the determining.

In some embodiments, provided is a non-transitory computer-readable recording medium with an executable program stored thereon. The program is an operation program of an image processing device and causes a computer to execute: acquiring a plurality of images that are captured with a same angle of view and are different from each other in a wavelength band of illumination light; determining, based on a first image and a second image different from the first image in the plurality of images, whether a first light absorber in a living body in the first image and a second light absorber in a living body in the second image overlap in a depth direction of a living body in the images; and extracting light-absorption information as a result of absorption by the first light absorber, by using the first image and the second image and a determination result obtained by the determining.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2 is a flowchart illustrating image processing executed by the image processing device according to an embodiment of the disclosure;

FIG. 4 is a flowchart illustrating light-absorption information overlapping determination processing according to an embodiment of the disclosure;

FIG. 5 is a flowchart illustrating light-absorption information extraction processing according to an embodiment of the disclosure;

DETAILED DESCRIPTION

Figure 1:
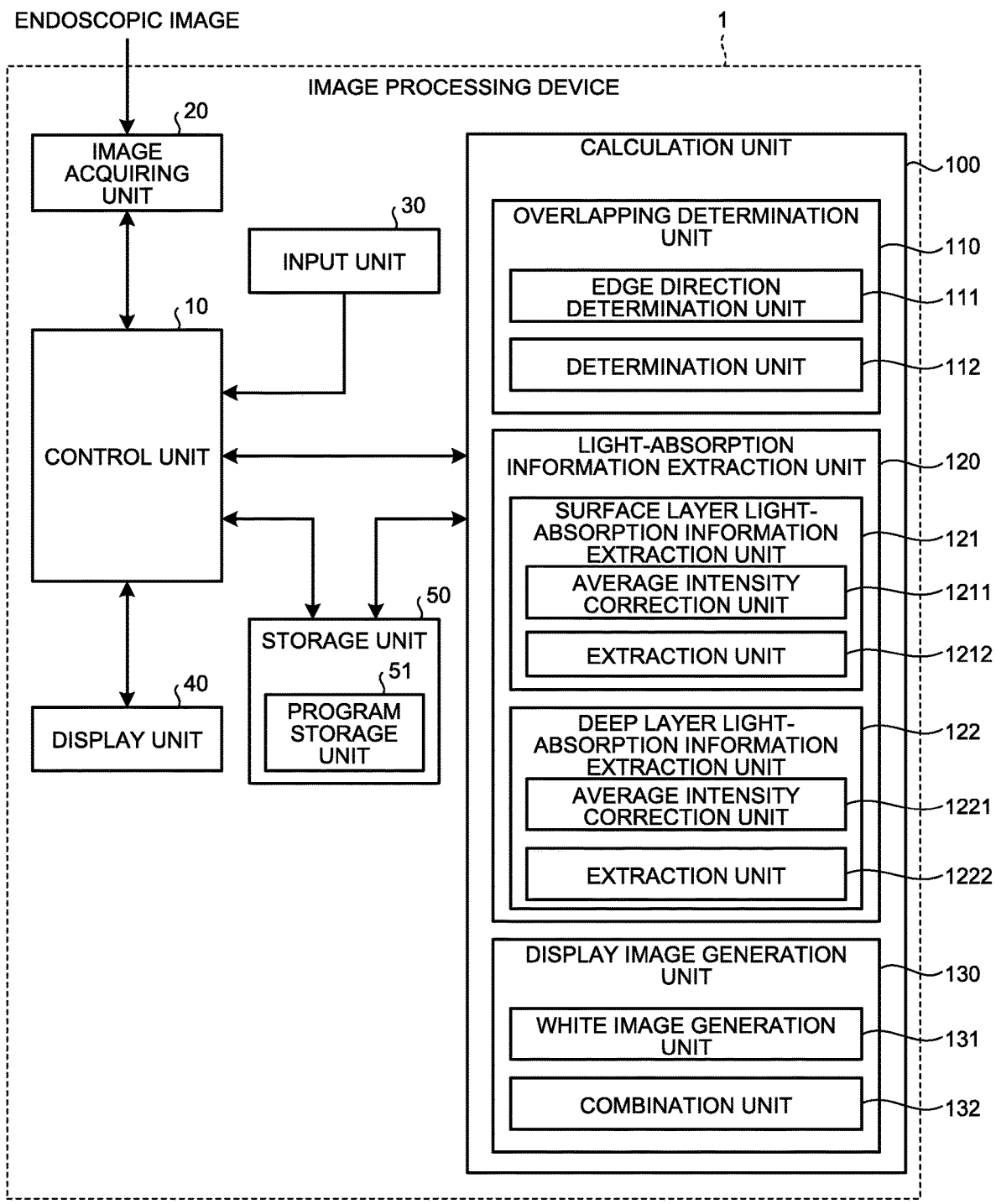
FIG. 1 is a block diagram illustrating a functional configuration of an image processing device according to an embodiment of the disclosure.

Hereinafter, an image processing device, an operation method of the image processing device, and an operation program for the image processing device according to an embodiment of the disclosure will be described with reference to the drawings. Note that the disclosure is not limited by these embodiments. Furthermore, the drawings are illustrated with the same parts denoted by the same reference numerals.

Embodiment

FIG. 1 is a block diagram illustrating a functional configuration of an image processing device according to an embodiment of the disclosure. An image processing device 1 according to the present embodiment extracts an absorption change, which hardly appears in a white image, based on a plurality of images acquired by the endoscope, and combines the extracted absorption change with one or more images to generate an image to be displayed. In the present embodiment, an absorption change as a result of absorption of a blood vessel that is a light absorber is extracted as light-absorption information.

In the following description, a target of processing is endoscopic images, including a plurality of images captured with different center wavelengths, obtained by capturing images inside a living body (for example, intraluminal images) with a capsule endoscope or a general endoscope known as a video scope. In the following, as an example, processing executed with images in a plurality of wavelength bands with different center wavelengths acquired will be described.

The present embodiment is given under an assumption that an endoscopic image is obtained by sequentially emitting light beams of five wavelength bands having center wavelengths of 415 nm, 460 nm, 540 nm, 600 nm, and 630 nm. In this specification, a description is given under an assumption that a plurality of images of different types of narrow band light beams, are captured with narrow band light beams of different center wavelengths. Hereinafter, an image captured by light in a wavelength band with a center wavelength of X nm will be referred to as a $\lambda_X$ image. Specifically, an image with a center wavelength of 415 nm is referred to as a $\lambda_{415}$ image, an image with a center wavelength 460 nm is referred to as a $\lambda_{460}$ image, an image with a center wavelength 540 nm is referred to as a $\lambda_{540}$ image, an image with a center wavelength 600 nm is referred to as a $\lambda_{600}$ image, and an image with a center wavelength of 630 nm is referred to as a $\lambda_{630}$ image. The $\lambda_{460}$ image, the $\lambda_{540}$ image, and the $\lambda_{630}$ image are images for generating a white image corresponding to the RGB wavelength band. The $\lambda_{415}$ image and the $\lambda_{600}$ image are images used for combination. The $\lambda_{415}$ image, the $\lambda_{460}$ image, the $\lambda_{540}$ image, the $\lambda_{600}$ image, and the $\lambda_{630}$ image are images with the same angle of view. Here, light of a wavelength around 415 nm is likely to be absorbed by hemoglobin and to be scattered by the mucosa in a lumen. In addition, light of a wavelength around 630 nm is less likely to be absorbed by hemoglobin and scattered by the mucosa, and thus has a characteristic of being likely to reach deep in the lumen. Thus, based on such a difference in optical characteristics or specific bands, a change in a signal value due to a regional absorption change and the like caused by microvessels in the mucosa surface layer and arteries in the mucosa deep layer, can be extracted from the image as light-absorption information. These images are acquired by an endoscope with, for example, light beams sequentially emitted from Light Emitting Diodes (LEDs) that emits light beams of wavelength bands with the center wavelengths, to illuminate the inside of the subject. The illumination light is not limited to the LEDs. For example, an image with each center wavelength may be acquired using a white light source and a filter that transmits light in a specific wavelength band, or by using a laser light source that emits light beams in the wavelength bands with the center wavelength.

As illustrated in FIG. 1, the image processing device 1 includes a control unit 10 that controls the overall operation of the image processing device 1, an image acquiring unit 20 that acquires image data of an endoscopic image, an input unit 30 that generates an input signal in response to an external operation, a display unit 40 that displays various contents, a storage unit 50 that stores the image data acquired by the image acquiring unit 20 and various programs, and a calculation unit 100 that executes predetermined image processing on the image data.

The control unit 10 is formed by using a general-purpose processor such as a central processing unit (CPU) or a dedicated processor such as various arithmetic circuits that execute specific functions such as an application specific integrated circuit (ASIC). When the control unit 10 is a general-purpose processor, the control unit 10 reads various programs stored in the storage unit 50 to transmit instructions and data to the units of the image processing device 1, and thus controls the entire operation of the image processing device 1. When the control unit 10 is a dedicated processor, the processor may independently execute various processes, or may use various data stored in the storage unit 50 and thus may cooperate with or be combined with the storage unit 50 to execute various types of processing.

The image acquiring unit 20 is appropriately configured in accordance with a mode of a system including the endoscope. For example, when connecting to the image processing device 1 of the general endoscope system with a videoscope to be inserted into a body, the image acquiring unit 20 is formed by an interface with which image data generated in the endoscope system is captured. When a server for storing image data generated in the endoscope system is installed, the image acquiring unit 20 is formed by a communication device or the like connected to the server, and performs data communications with the server to obtain an image. Alternatively, in the case of using a capsule endoscope that captures images while moving in a living body, image data may be exchanged between a portable storage medium and the capsule endoscope. In such a case, the image acquiring unit 20 is formed by a reader that has the portable storage medium mounted thereon and reads out image data of a stored image.

The input unit 30 includes, for example, input devices such as a keyboard, a mouse, a touch panel, and various switches, and outputs, to the control unit 10, an input signal generated in response to an external operation on these input devices.

The display unit 40 is formed by a display device such as a liquid crystal display (LCD) or an electroluminescence (EL) display, and displays various screens including an endoscopic image under the control of the control unit 10.

The storage unit 50 includes an information storage device, a device that writes and reads information to and from the information storage device, and the like. The information storage device includes various IC memories such as read only memory (ROM) and a random access memory (RAM) such as a flash memory capable of updating and recording, as well as a built-in element or an element connected through a data communication terminal such as a hard disk or a CD-ROM. The storage unit 50 stores image data of an endoscopic image acquired by the image acquiring unit 20 as well as a program for operating the image processing device 1 and causing the image processing device 1 to execute various functions, data used while the programs are executed, and the like. Specifically, the storage unit 50 includes a program storage unit 51 that stores an operation program for the image processing device 1 that causes the image processing device 1 to execute image processing for emphasizing one or a plurality of narrow band images to generate an emphasized image, based on a plurality of narrow band images that are acquired by the endoscope and have different wavelength component distributions.

The calculation unit 100 is formed by a general purpose processor such as a CPU or a dedicated processor such as various calculation circuits that execute a specific function such as an ASIC. When the calculation unit 100 is a general purpose processor, the processor executes image processing by reading an image processing program stored in the program storage unit 51. When the calculation unit 100 is a dedicated processor, the processor may independently execute various processes, or may use various data stored in the storage unit 50 and thus may cooperate with or be combined with the storage unit 50 to execute image processing.

Next, a configuration of the calculation unit 100 will be described. As illustrated in FIG. 1, the calculation unit 100 includes an overlapping determination unit 110, a light-absorption information extraction unit 120, and a display image generation unit 130. The overlapping determination unit 110 determines whether a visualized target overlaps based on endoscopic images acquired by the image acquiring unit 20. The light-absorption information extraction unit 120 extracts light-absorption information at a predetermined depth from the mucosa. The display image generation unit 130 generates a display image based on the light-absorption information thus extracted.

The overlapping determination unit 110 includes an edge direction determination unit 111 and a determination unit 112. The edge direction determination unit 111 determines the edge direction for each pixel of each image. The determination unit 112 determines whether the target (a blood vessel in this case) overlaps, in a depth direction in the living body, in the $\lambda_{415}$ image and the $\lambda_{540}$ image, and determines whether the target (a vessel in this case) overlaps, in the depth direction in the living body, in the $\lambda_{540}$ image and the $\lambda_{600}$ image, based on the determination result obtained by the edge direction determination unit 111. Here, the depth direction in the living body in the image is a direction corresponding to a direction orthogonal to the imaging plane.

The light-absorption information extraction unit 120 includes a surface layer light-absorption information extraction unit 121 that extracts the light-absorption information about the surface layer, and a deep layer light-absorption information extraction unit 122 that extracts light-absorption information about the deep layer.

The surface layer light-absorption information extraction unit 121 includes an average intensity correction unit 1211 and an extraction unit 1212. The average intensity correction unit 1211 corrects an average intensity of the $\lambda_{415}$ image in accordance with the average intensity of the $\lambda_{540}$ image. The extraction unit 1212 extracts light-absorption information about the surface layer by using the intensities of the $\lambda_{415}$ image and the $\lambda_{540}$ image.

The deep layer light-absorption information extraction unit 122 includes an average intensity correction unit 1221 and an extraction unit 1222. The average intensity correction unit 1221 corrects an average intensity of the $\lambda_{600}$ image in accordance with the average intensity of the $\lambda_{540}$ image. The extraction unit 1222 extracts light-absorption information about the surface layer by using the intensities of the $\lambda_{600}$ image and the $\lambda_{540}$ image.

The display image generation unit 130 includes a white image generation unit 131 that generates a white image from a plurality of images different from each other in the center wavelength, and a combination unit 132 that combines the white image with an image corresponding to the light-absorption information extracted by the light-absorption information extraction unit 120.

Next, an operation of the image processing device 1 will be described. FIG. 2 is a flowchart illustrating image processing executed by the image processing device 1. First of all, in step S10, the image acquiring unit 20 acquires a plurality of images different from each other in the center wavelength. Specifically, the image acquiring unit 20 sequentially acquires the five images, which are the $\lambda_{415}$ image, the $\lambda_{460}$ image, the $\lambda_{540}$ image, the $\lambda_{600}$ image, and the $\lambda_{630}$ image, captured using light beams of the respective wavelength bands with the center wavelength of 415 nm, 460 nm, 540 nm, 600 nm, and 630 nm.

As an example of the method of acquiring these images by an endoscope, LEDs may be used for illumination. For example, five LEDs emitting light in five respective wavelength bands with the center wavelengths of 415 nm, 460 nm, 540 nm, 600 nm and 630 nm are provided. The LEDs sequentially emit light to illuminate the inside of a living body, and reflected light from the inside of the living body is acquired for each narrow band by an image sensor of the corresponding color. As a result, five images can be obtained with the center wavelengths of 415 nm, 460 nm, 540 nm, 600 nm and 630 nm. The actual center wavelengths of the light beams with which these images are acquired may be values near 415 nm, 460 nm, 540 nm, 600 nm, and 630 nm described above.

Figure 3A:
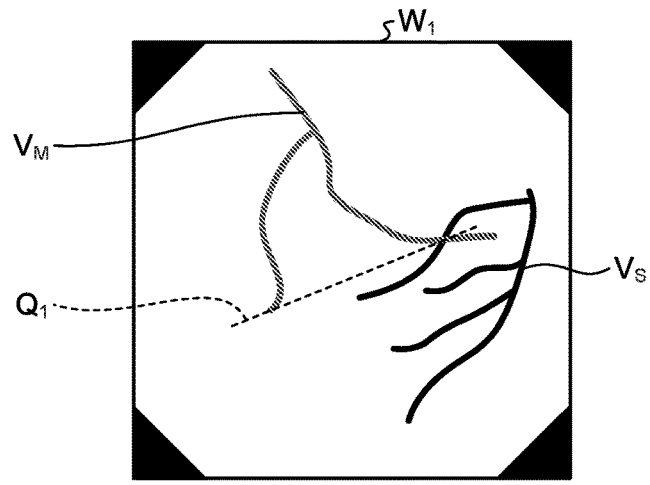
FIG. 3A is a diagram illustrating an image acquired in image processing executed by the image processing device according to an embodiment of the disclosure.
Figure 3B:
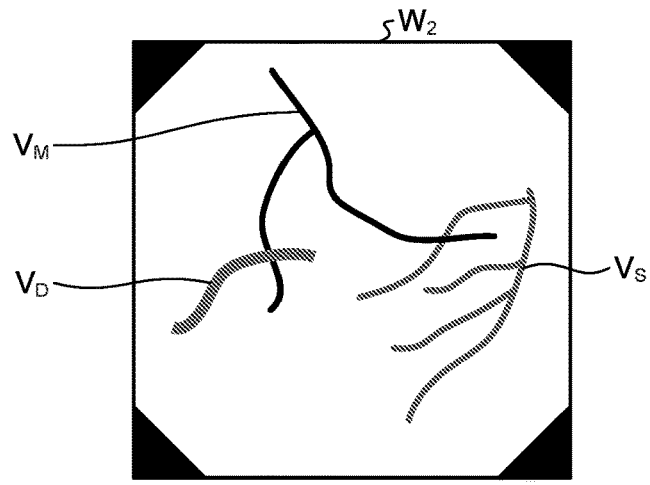
FIG. 3B is a diagram illustrating an image acquired in image processing executed by the image processing device according to an embodiment of the disclosure.
Figure 3C:
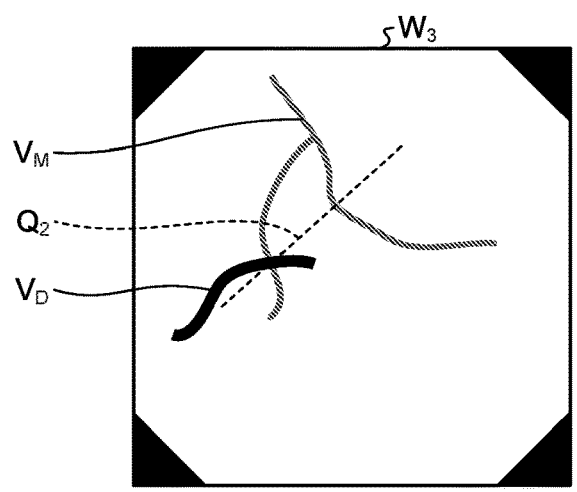
FIG. 3C is a diagram illustrating an image acquired in image processing executed by the image processing device according to an embodiment of the disclosure.

Here, blood vessel images visualized in the $\lambda_{415}$ image, the $\lambda_{540}$ image, and the $\lambda_{600}$ image will be described with reference to FIGS. 3A to 3C. FIGS. 3A to 3C are diagrams illustrating images acquired in image processing executed by the image processing device according to an embodiment of the disclosure. FIG. 3A illustrates a $\lambda_{415}$ image. FIG. 3B illustrates a $\lambda_{540}$ image. FIG. 3C illustrates a $\lambda_{600}$ image. As described above, the light in the vicinity of 415 nm is likely to be absorbed by hemoglobin and to be scattered by the mucosa of a lumen. Thus, a $\lambda_{415}$ image $W_1$ based on this light has a surface layer blood vessel $V_S$ clearly visualized, and has a middle layer blood vessel $V_M$ not clearly but visualized (see FIG. 3A). On the other hand, light in the vicinity of 630 nm is less likely to be absorbed by hemoglobin and to be scattered in the mucosa, and thus is likely to reach deep into the lumen. Thus, a $\lambda_{600}$ image $W_3$ based on this light has a deep layer blood vessel $V_D$ clearly visualized, and the middle layer blood vessel $V_M$ not clearly but visualized (see FIG. 3C). In addition, in a $\lambda_{540}$ image $W_2$ based on light of 540 nm between 415 nm and 600 nm, the middle layer blood vessel $V_M$ is clearly visualized, and the surface layer blood vessel $V_S$ and the deep layer blood vessel $V_D$ are not clearly but visualized (see FIG. 3B). The deep layer blood vessel $V_D$ is not visualized in the $\lambda_{415}$ image $W_1$, and the surface layer blood vessel $V_S$ is not visualized in the $\lambda_{600}$ image $W_3$.

In the next step S20, the overlapping determination unit 110 determines whether the light-absorption information overlaps, that is, whether blood vessels overlap in the depth direction between the $\lambda_{415}$ image and the $\lambda_{540}$ image, and whether blood vessels overlap in the depth direction in the $\lambda_{540}$ image and the $\lambda_{600}$ image. FIG. 4 is a flowchart illustrating light-information overlapping determination processing according to an embodiment of the disclosure.

In step S21, the edge direction determination unit 111 determines the edge direction for each pixel of the $\lambda_{415}$ image, the $\lambda_{540}$ image, and the $\lambda_{600}$ image. For example, the edge direction determination unit 111 classifies the edge determination results for each pixel into five categories including horizontal direction (Hor), vertical direction (Ver), upper left direction (Hv1), upper right direction (Hv2), and flat (no edge). The edge direction determination unit 111 first calculates an edge amount Tmp in each direction using the following Formula (1):

$$\text{Tmp}\_{Hor} = |I_{415}(x,y) - I_{415}(x-1,y)| + |I_{415}(x,y) - I_{415}(x+1,y)|$$

$$\text{Imp}\_{ver} = |I_{415}(x,y) - I_{415}(x,y-1)| + |I_{415}(x,y) - I_{415}(x,y+1)|$$

$$\text{Tmp}\_{Hv1} = |I_{415}(x,y) - I_{415}(x-1,y+1)| + |I_{415}(x,y) - I_{415}(x+1,y-1)|$$

$$\text{Tmp}\_{Hv2} = |I_{415}(x,y) - I_{415}(x-1,y-1)| + |I_{415}(x,y) - I_{415}(x+1,y+1)| \quad (1).$$

In the formula, X represents the horizontal coordinate of the image (with the positive side corresponding to the right direction), Y represents the vertical coordinate of the image (with the positive side corresponding to the downward direction),

|a| represents an absolute value of a, and $I_{415}(x,y)$ represents a signal value of coordinates (x,y) of $\lambda_{415}$ image.

The edge direction determination unit 111 similarly calculates the edge amount for the $\lambda_{540}$ image and the $\lambda_{600}$ image.

Thereafter, the edge direction determination unit 111 determines the edge direction at the coordinates (x,y) based on the maximum value of the four types of edge amounts described above, and provides an edge determination value $(\text{Ori}_{415}(x,y))$ corresponding to the determined edge direction in accordance with the following conditions.

Maximum edge amount Edge determination $(\text{Ori}_{415}(x,y))$

Tmp$\_{Hor}$ 0 (edge direction: horizontal direction)

Tmp$\_{Ver}$ 1 (edge direction: vertical direction)

Imp$\_{Hv1}$ 2 (edge direction: upper left)

Imp$\_{Hv2}$ 3 (edge direction: upper right)

Note that, when the maximum value of the edge amount is less than a threshold, the edge direction determination unit 111 determines that there is no edge (flat portion), and sets the edge determination value $\text{Ori}_{415}(x,y)$ to 4.

The edge direction determination unit 111 similarly determines the edge direction also for the $\lambda_{540}$ image and the $\lambda_{600}$ image, and provides edge determination values $\text{Ori}_{540}(x,y)$ and $\text{Ori}_{600}(x,y)$.

In the next step S22, the determination unit 112 uses the edge determination values $\text{Ori}_{415}(x,y)$ and $\text{Ori}_{540}(x,y)$ to determine whether blood vessels overlap in the $\lambda_{415}$ image and the $\lambda_{540}$ image in the depth direction (in this case, the surface layer blood vessel and the middle layer blood vessel). Specifically, the determination unit 112 determines whether the blood vessels overlap in the following manner based on the edge determination values.

Surface Layer Blood Vessel and Middle Layer Blood Vessel Do Not Overlap

The determination unit 112 refers to the determination values $\text{Ori}_{415}(x,y)$ and $\text{Ori}_{540}(x,y)$, and if the edge determination values are the same or at least one of the edge determination values is 4, the surface layer blood vessel and the middle layer blood vessel are determined to be not overlapped at the coordinates.

Surface Layer Blood Vessel and Middle Layer Blood Vessel Overlap

If the edge determination values are different from each other and are in a range between 0 and 3, the determination unit 112 determines that the surface layer blood vessel and the middle layer blood vessel overlap at the coordinates.

The determination unit 112 sets an overlapping determination value $\text{Flag}_{415}(x,y)$ to 0 upon determining that the surface layer blood vessel and the middle layer blood vessel do not overlap in the $\lambda_{415}$ image and the $\lambda_{540}$ image, and sets the overlapping determination value $\text{Flag}_{415}(x,y)$ to 1 upon determining that the middle layer blood vessel and the deep layer blood vessel overlap.

In the next step S23, the determination unit 112 uses the edge determination values $\text{Ori}_{540}(x,y)$ and $\text{Ori}_{600}(x,y)$ to determine whether blood vessels overlap in the $\lambda_{540}$ image and the $\lambda_{600}$ image in the depth direction (in this case, the middle layer blood vessel and the deep layer blood vessel). Specifically, the determination unit 112 determines whether the blood vessels overlap in the following manner based on the edge determination values.

Middle Layer Blood Vessel And Deep Layer Blood Vessel Do Not Overlap

The determination unit 112 refers to the determination values $Ori_{540}(x,y)$ and $Ori_{600}(x,y)$, and if the edge determination values are the same or at least one of the edge determination values is 4, the blood vessels are determined to be not overlapped at the coordinates.

Middle Layer Blood Vessel and Deep Layer Blood Vessel Overlap

If the edge determination values are different from each other and are in a range between 0 and 3, it is determined that there is the overlap in the $\lambda_{540}$ image and the $\lambda_{600}$ image at the coordinates.

The determination unit 112 sets an overlapping determination value $Flag_{600}(x,y)$ to 0 upon determining that there is no overlap of the blood vessels, and sets the overlapping determination value $Flag_{600}(x,y)$ to 1 upon determining that there is the overlap of the blood vessels Referring back to FIG. 2, in step S30, the light-absorption information extraction unit 120 extracts light-absorption information about the surface layer and about the deep layer of the mucosa. FIG. 5 is a flowchart illustrating light-absorption information extraction processing according to an embodiment of the disclosure.

In step S31, the light-absorption information extraction unit 120 calculates the average intensity of the $\lambda_{415}$ image, the average intensity of the $\lambda_{540}$ image, and the average intensity of the $\lambda_{600}$ image. The light-absorption information extraction unit 120 may calculate the average intensity from the entire image, or may calculate the average intensity from an area set in advance.

In the next step S32, the average intensity correction unit 1211 corrects the intensity of the $\lambda_{415}$ image according to the average intensity of the $\lambda_{540}$ image. The average intensity correction unit 1211 corrects the intensity of the $\lambda_{415}$ image based on the ratio of the average intensity of the $\lambda_{415}$ image to the average intensity of the $\lambda_{540}$ image. Thus, the brightness of the $\lambda_{415}$ image is corrected. Furthermore, in step S32, the average intensity correction unit 1221 corrects the intensity of the $\lambda_{600}$ image according to the average intensity of the $\lambda_{540}$ image. The average intensity correction unit 1221 corrects the intensity of the $\lambda_{600}$ image based on the ratio of the average intensity of the $\lambda_{600}$ image to the average intensity of the $\lambda_{540}$ image. Thus, the brightness of the $\lambda_{600}$ image is corrected. In the present embodiment, the brightness corresponds to the pixel value in each pixel.

Figure 6:
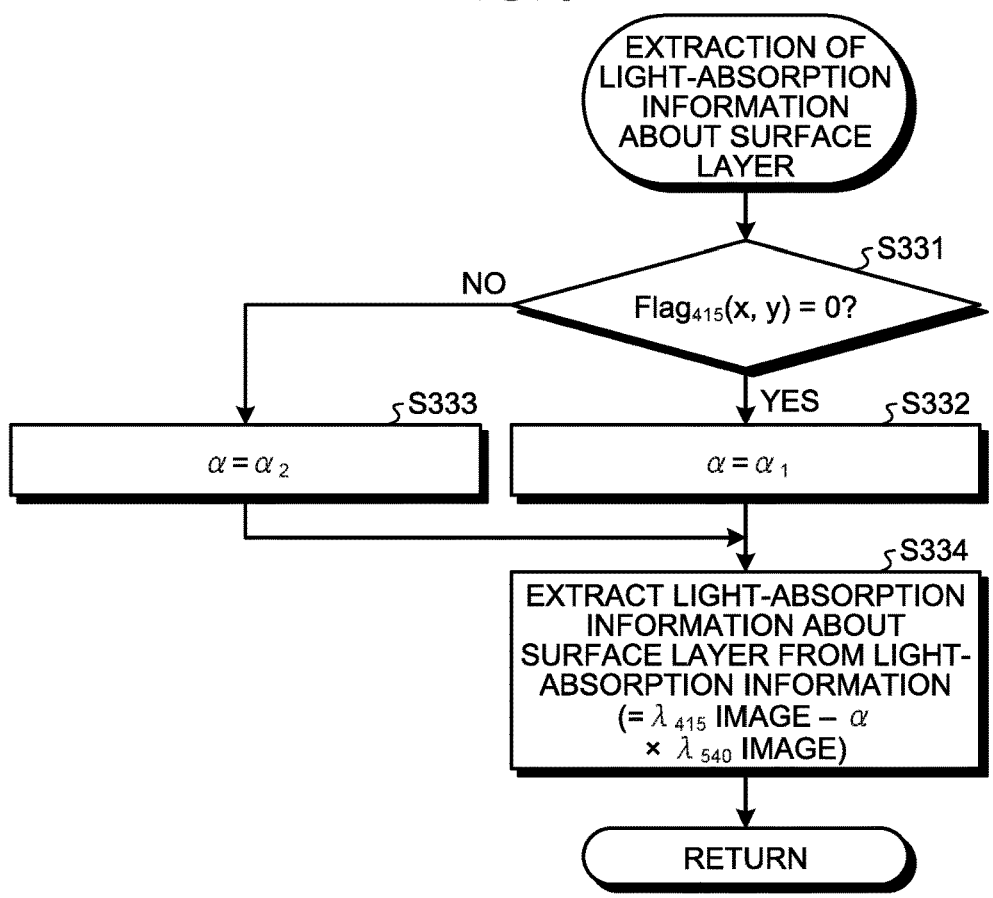
FIG. 6 is a flowchart illustrating processing of extracting light-absorption information about a surface layer according to an embodiment of the disclosure.

In the next step S33, the extraction unit 1212 extracts light-absorption information about the surface layer. FIG. 6 is a flowchart illustrating processing of extracting light-absorption information about a surface layer according to an embodiment of the disclosure.

In step S331, the extraction unit 1212 refers to the determination result (overlapping determination value $Flag_{415}(x,y)$) obtained by the determination unit 112, and determines whether there is an overlap at the coordinates (x,y). When the extraction unit 1212 determines that the surface layer blood vessel and the middle layer blood vessel do not overlap, that is, when the overlap determination value $Flag_{415}(x,y)=0$ (step S331: Yes), the processing proceeds to step S332. On the other hand, when the extraction unit 1212 determines that there is the overlap of the blood vessels, that is, when the overlap determination value $Flag_{415}(x,y)=1$ (step S331: No), the processing proceeds to step S333.

In step S332, the extraction unit 1212 sets a coefficient α for extracting light-absorption information to $\alpha_1$. In the present embodiment, $\alpha_1$ is set in advance, that is, $\alpha_1=1$.

In step S333, the extraction unit 1212 sets the coefficient α for extracting light-absorption information to $\alpha_2$. In the present embodiment, $\alpha_2$ is set in advance, that is, $\alpha_2>1$. Note that $\alpha_2$ may be any number larger than $\alpha_1$. Furthermore, $\alpha_2$ may be calculated from a pixel value of a pixel of the $\lambda_{540}$ image and pixel values of pixels around the pixel. For example, a ratio between a pixel value of a pixel that is a setting target in the $\lambda_{540}$ image and a pixel value (an average value for example) of a pixels in the periphery (5×5 pixels around the pixel as the setting target) is obtained to be set as the coefficient $\alpha_2$, or a ratio between the pixel value of the pixel that is the setting target and a pixel value of a peripheral pixel determined to be free of overlapping is set to be the coefficient $\alpha_2$.

By executing the above-described processing on each pixel position (coordinates (x, y)), the coefficient α ($\alpha_1$ or $\alpha_2$) is provided to each pixel position.

When the coefficient α is set in step S332 or step S333, the extraction unit 1212 calculates light-absorption information (step S334). The extraction unit 1212 subtracts the pixel value of the $\lambda_{540}$ image multiplied by a ($\alpha_1$ or $\alpha_2$) from the pixel value of the $\lambda_{415}$ image based on the $\lambda_{415}$ image and $\lambda_{540}$ image after intensity correction, and extracts a pixel with the subtraction result of a negative value. Thus, the light-absorption information about the surface layer is extracted.

Figure 7:
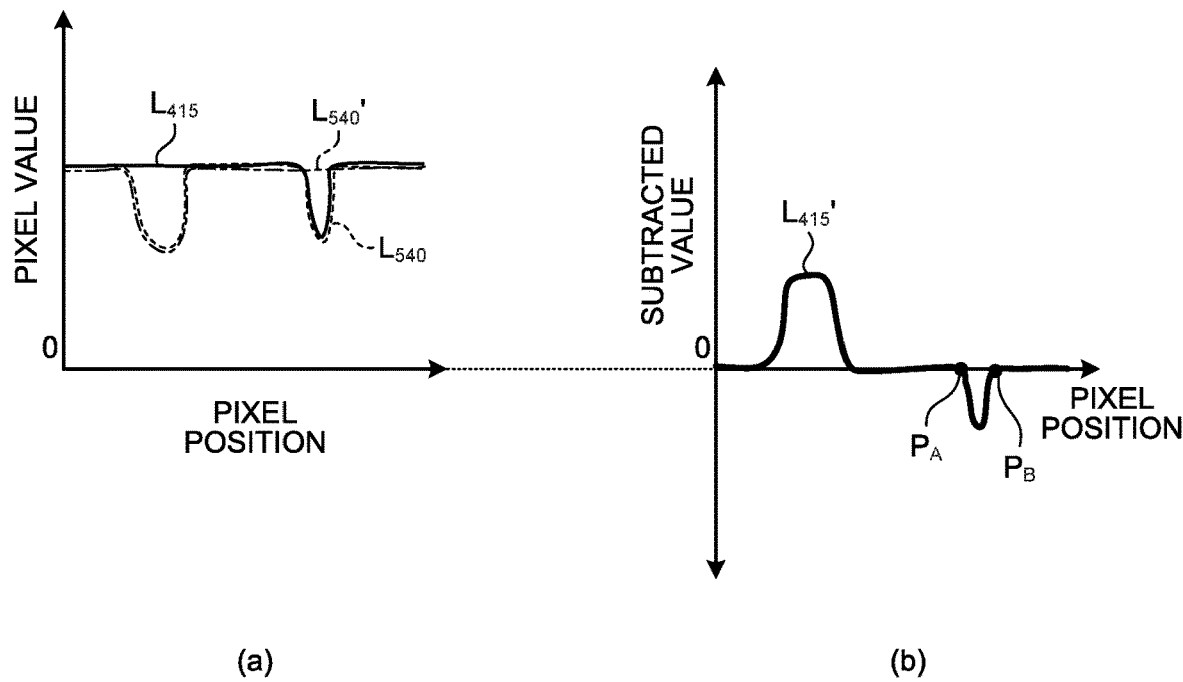
FIG. 7 is a diagram illustrating processing of extracting light-absorption information about a surface layer according to an embodiment of the disclosure.

FIG. 7 is a diagram illustrating processing of extracting light-absorption information about a surface layer according to an embodiment of the disclosure. FIG. 7 is a diagram illustrating an example of relationship between a pixel position on a certain line (here, a broken line $Q_1$ illustrated in FIG. 3A) and a pixel value at that pixel position. In (a) of FIG. 7, a curve $L_{415}$ represents the pixel values of the $\lambda_{415}$ image, a curve $L_{540}$ represents the pixel values of the $\lambda_{540}$ image before multiplication by the coefficient α, and a curve $L_{540}'$ represents pixel values of the $\lambda_{540}$ image after the multiplication by the coefficient α ($\alpha_1$ or $\alpha_2$). The coefficient $\alpha_2$ for the multiplication for the curve $L_{540}'$ is a value (for example, the above-described ratio) adaptively set according to the pixel value of the pixel position. By subtracting the pixel value (curve $L_{540}'$) of the $\lambda_{540}$ image multiplied by the coefficient α ($\alpha_1$ or $\alpha_2$) from the pixel value (curve $L_{415}$) of the $\lambda_{415}$ image, a light-absorption information extraction curve $L_{415}'$ of the $\lambda_{415}$ image is obtained (see in (b) of FIG. 7). In the $\lambda_{540}$ image multiplied by the coefficient α ($\alpha_1$ or $\alpha_2$), it is determined that there is the overlap in step S331 described above, and the pixel value for which the coefficient is set to $\alpha_2$ is larger than the pixel value of the $\lambda_{415}$ image. The extraction unit 1212 extracts a pixel having a negative value from the light-absorption information extraction curve $L_{415}'$. In this process, a threshold may be set in advance and pixels below this threshold may be extracted. In the light-absorption information extraction curve $L_{415}'$ illustrated in (b) FIG. 7, a pixel $P_A$ to a pixel $P_B$ are extracted, and the extraction unit 1212 generates light-absorption information in which extracted pixel positions and values (negative values) at the pixel positions are associated. In (b) of FIG. 7, the pixel $P_A$ to the pixel $P_B$ extracted are extracted as a portion in which the surface layer blood vessel and the middle layer blood vessel overlap.

On the other hand, conventionally, the pixel value (e.g., the curve $L_{540}$) of the $\lambda_{540}$ image is uniformly subtracted from the pixel value of the $\lambda_{415}$ image without multiplying the pixel value of the overlap portion of the $\lambda_{540}$ image by the coefficient (>1). Thus, the overlapping portion would not be extracted as the negative values, and thus the overlapping portion may lack in the resultant light-absorption information.

Figure 8:
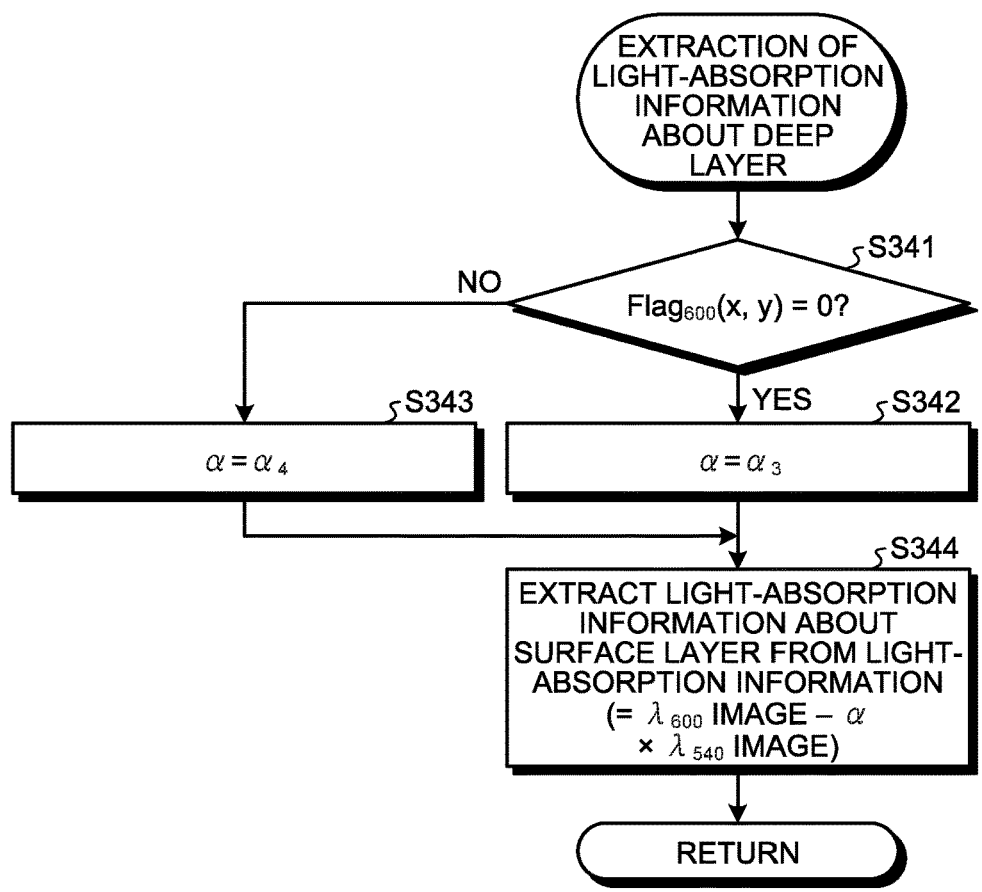
FIG. 8 is a flowchart illustrating processing of extracting light-absorption information about a deep layer according to an embodiment of the disclosure.

In the next step S34, the extraction unit 1222 extracts light-absorption information about the deep layer. FIG. 8 is a flowchart illustrating processing of extracting light-absorption information about a deep layer according to an embodiment of the disclosure.

In step S341, the extraction unit 1222 refers to the determination result (overlapping determination value $Flag_{600}(x,y)$) obtained by the determination unit 112, and determines whether there is an overlap at the coordinates (x,y). When the extraction unit 1222 determines that the middle layer blood vessel and the deep layer blood vessel do not overlap, that is, when the overlap determination value $Flag_{600}(x,y)=0$ (step S341: Yes), the processing proceeds to step S342. On the other hand, when the extraction unit 1222 determines that there is the overlap of the blood vessels, that is, when the overlap determination value $Flag_{600}(x,y)=1$ (step S341: No), the processing proceeds to step S343.

In step S342, the extraction unit 1222 sets the coefficient α for extracting light light-absorption information to $α_3$. In the present embodiment, $α_3$ is set in advance, that is, $α_3=1$.

In step S343, the extraction unit 1222 sets the coefficient α for extracting light light-absorption information to $α_4$. In the present embodiment, $α_4$ is set in advance, that is, $α_4>1$. Note that $α_4$ may be any number larger than $α_3$. Furthermore, $α_4$ may be calculated from a pixel value of a pixel that is a setting target and pixel values of pixels around the pixel, as in the case of $α_2$.

By executing the above-described processing on each pixel position (coordinates (x, y)), the coefficient α ($α_3$ or $α_4$) is provided to each pixel position.

When the coefficient α is set in step S342 or step S343, the extraction unit 1222 calculates light-absorption information (step S344). The extraction unit 1222 subtracts the pixel value of the $λ_{600}$ image multiplied by a ($α_3$ or $α_4$) from the pixel value of the $λ_{540}$ image based on the $λ_{540}$ image and $λ_{600}$ image after intensity correction, and extracts a pixel with a negative value. Thus, the light-absorption information about the deep layer is extracted. The extraction unit 1222 generates light-absorption information in which the extracted pixel position is associated with the value (negative value) at the pixel position, through an operation similar to that by the extraction unit 1212.

Figure 9:
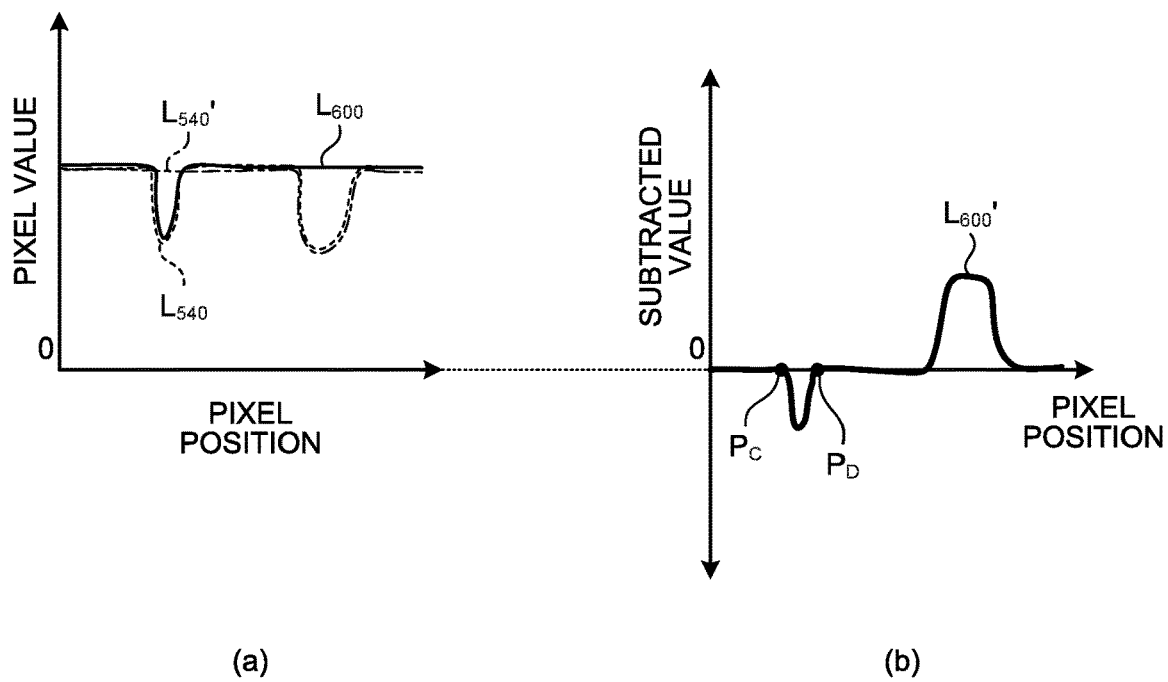
FIG. 9 is a diagram illustrating processing of extracting light-absorption information about a deep layer according to an embodiment of the disclosure.

FIG. 9 is a diagram illustrating processing of extracting light-absorption information about a surface layer according to an embodiment of the disclosure. FIG. 9 is a diagram illustrating an example of relationship between a pixel position on a certain line (here, a broken line $Q_2$ illustrated in FIG. 3C) and a pixel value at that pixel position. In (a) of FIG. 9, a curve $L_{600}$ represents the pixel values of the $λ_{600}$ image, a curve $L_{540}$ represents the pixel values of the $λ_{540}$ image, and a curve $L_{540}'$ represents pixel values of the $λ_{540}$ image after the multiplication by the coefficient α ($α_3$ or $α_4$). The coefficient $α_4$ for the multiplication for the curve $L_{540}'$ is a value adaptively set according to the pixel value of the pixel position. By subtracting the pixel value (curve $L_{540}'$) of the $λ_{540}$ image multiplied by the coefficient α ($α_3$ or ao from the pixel value of the $λ_{600}$ image, a light-absorption information extraction curve $L_{600}'$ of the $λ_{600}$ image is obtained (see (b) of FIG. 9). In the $λ_{540}$ image multiplied by the coefficient α ($α_3$ or $α_4$), it is determined that there is the overlap in step S331 described above, and the pixel value for which the coefficient is set to $α_4$ is larger than the pixel value of the $λ_{600}$ image. The extraction unit 1222 extracts a pixel having a negative value from the light-absorption information extraction curve $L_{600}'$. In this process, a threshold may be set in advance and pixels below this threshold may be extracted. In the light-absorption information extraction curve $L_{600}'$ illustrated in (b) of FIG. 9, a pixel $P_C$ to a pixel $P_D$ are extracted, and the extraction unit 1212 generates light-absorption information in which extracted pixel positions and values (negative values) at the pixel positions are associated. In of (b) of FIG. 9, the extracted pixels $P_C$ to $P_D$ involve the overlapping of the middle layer blood vessel and the deep layer blood vessel and are extracted as a portion corresponding to the deep layer blood vessel. Specifically, a convex portion with small subtracted values corresponds to the overlapping portion.

In addition, step S33 and step S34 described above may be performed with step S34 performed earlier or with step S33 and step S34 simultaneously performed.

In step S40 following step S30, the display image generation unit 130 generates a display image obtained by combining the light-absorption information with the white image. Specifically, first, the white image generation unit 131 generates the white image using the $λ_{460}$ image, the $λ_{540}$ image, and the $λ_{630}$ image that correspond to the RGB wavelength bands acquired in step S10. The white image generation unit 131 determines the pixel value of each pixel in the white image by setting the $λ_{460}$ image as a B component, the $λ_{540}$ image as a G component, and the $λ_{630}$ image as an R component. Then, the combination unit 132 combines the white image with the light-absorption information about the $λ_{415}$ image serving as the B component and combines the light-absorption information about the $λ_{600}$ image serving as the R component among the light-absorption information acquired in step S30. In this process, for example, when the light-absorption information about the surface layer (the light-absorption information about the $λ_{415}$ image) is combined as the B component, the B component at the relevant position decreases and the color changes from blue to be close to yellow, whereby the blood vessel in the surface layer is visualized. On the other hand, when the light-absorption information about the deep layer (the light-absorption information about the $λ_{600}$ image) is combined as the R component, the R component at the relevant position decreases and the color changes from red to be close to cyan, whereby the blood vessel in the deep layer is visualized In addition, a method of combining the light-absorption information is not limited to this. For example, any piece of the light-absorption information may be combined as the G component. Furthermore, the light-absorption information may be combined with a preset ratio among the R component, the G component and the B component. Furthermore, when the white image is directly acquired in step S10, the combination unit 132 directly combines the light-absorption information with the white image.

In the embodiment described above, the overlapping of blood vessels in the $λ_{415}$ image and the $λ_{540}$ image, and the overlapping of blood vessels in the $λ_{540}$ image and the $λ_{600}$ image are determined, and the coefficient α used for extraction is determined based on the determination result. The subtraction processing is executed using α thus determined. The present embodiment can achieve an effect that blood vessels at a specific depth can be visualized without fail for images with blood vessels at different depths.

On the other hand, in the conventional processing, the processing was uniformly performed regardless of whether there is the overlapping of the light-absorption information. Specifically, for example, when extracting the light-absorption information about the surface layer, the coordinates at which the result of subtracting the $λ_{540}$ image from the $λ_{415}$ image is of a negative value (minus) is extracted as the light-absorption information about the surface layer. Therefore, in the conventional image, an area where the surface layer blood vessel $V_s$ and the middle layer blood vessel $V_M$ overlap, that is, an area between the pixel $P_A$ and the pixel $P_B$ in (a) of FIG. 7 for example fails to have the results of negative values, resulting in a lack of a part of the surface layer blood vessel $V_S$.

The wavelength band and the emission order of the light beams emitted, and the imaging means are not limited to those in the first embodiment described above, and an image not used for enhancement may be captured. For example, simultaneous emission of light beams in the wavelength bands with the center wavelengths of 415 nm, 540 nm, and 630 nm and simultaneous emission of light beams in the wavelength bands with the center wavelengths of 460 nm, 540 nm, and 600 nm may be alternatively repeated, and images may be captured using a Bayer sensor, a three-plate sensor, or the like. Furthermore, the light source to be used is not limited, and an LED, a xenon light source, a laser light source, or the like can be used.

In addition, other examples of methods of acquiring a narrow band image may be employed. Such methods include a method including arranging a filter in front of a white light source such as a xenon lamp and sequentially irradiating the inside of a living body with light with the wavelength band limited using the filter, and a method including sequentially driving a plurality of laser diodes that emit light beams different from each other in the center wavelength. Furthermore, an image may be obtained with the inside of the living body irradiated with white light, and with the reflected light from the living body made incident on an image sensor.

Modification of the Embodiment

Figure 10:
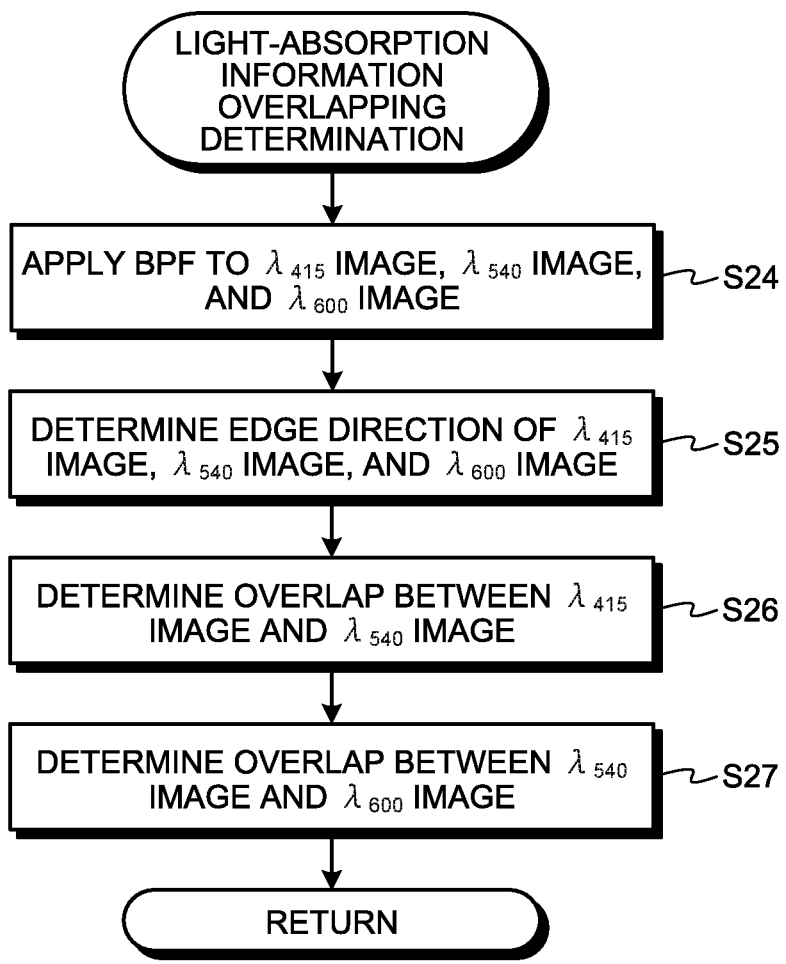
FIG. 10 is a flowchart illustrating light-absorption information extraction processing according to a modification of the embodiment of the disclosure.

Next, a modification of the embodiment of the disclosure will be described. In this modification, a band pass filter (BPF) is used for pre-processing in the above-described the light-absorption information overlap determination. FIG. 10 is a flowchart illustrating processing of extracting light-absorption information executed by an image processing device 1 according to the modification of the embodiment of the disclosure.

In step S24, the determination unit 112 extracts specific frequency components from the $\lambda_{415}$ image, the $\lambda_{540}$ image, and the $\lambda_{600}$ image using a band pass filter. Generally, the images include noise components, and thus there is a risk of false detection. If the band pass filter is used, it is possible to remove components (noise) other than the frequency band corresponding to the blood vessel. Thus, an improvement in detection accuracy in the edge direction can be expected. In this modification, the frequency band of the band pass filter is different among images. For example, many surface layer blood vessels visualized in the $\lambda_{415}$ image are thin (fine). Thus, the band of the band pass may be set to a high frequency range to facilitate the extraction of the characteristics of the surface layer blood vessels. For example, many deep layer blood vessels visualized in the $\lambda_{600}$ image are thick. Thus, the band of the band pass may be set to a low frequency range to facilitate the extraction of the characteristics of the deep layer blood vessels. A band pass filter having a common band of the band may be used for the purpose of removing noise only.

Thereafter, processing in step S25 and after is the same as the processing in steps S21 to S23 described above. Specifically, in step S25, the edge direction determination unit 111 determines the edge direction for pixels also in the $\lambda_{415}$ image, the $\lambda_{540}$ image, and the $\lambda_{600}$ image and provides edge determination values $Ori_{415}(x,y)$, $Ori_{540}(x,y)$, and $Ori_{600}(x,y)$ In the next step S26, the determination unit 112 uses the edge determination values $Ori_{415}(x,y)$ and $Ori_{540}(x,y)$ to determine whether blood vessels overlap in the $\lambda_{415}$ image and the $\lambda_{540}$ image in the depth direction, and provides the overlapping determination value $Flag_{415}(x,y)$.

In the next step S27, the determination unit 112 uses the edge determination values $Ori_{540}(x,y)$ and $Ori_{600}(x,y)$ to determine whether blood vessels overlap in the $\lambda_{540}$ image and the $\lambda_{600}$ image in the depth direction, and provides the overlapping determination value $Flag_{600}(x,y)$.

According to this modification described above, since the band pass filter (BPF) is used for the pre-processing in the light-absorption information overlapping determination, the edge direction can be detected more accurately.

Although the embodiments of the disclosure have been described above, the disclosure should not be limited to the above-described embodiments only. For example, in the embodiment described above, image acquired using light beams in five wavelength bands having respective center wavelengths of 415 nm, 460 nm, 540 nm, 600 nm, and 630 nm. Note that the disclosure is applicable to any images acquired using light beams of different types. Specifically, the disclosure is applicable to any images acquired using light beams different from each other in a distribution of wavelength components, that is, different from each other in the center wavelength. The disclosure may include various embodiments and the like not described herein.

In the above-described embodiment, the overlapping determination is performed for each pixel. However, a determination area including a plurality of pixels may be set, and the overlapping determination may be performed for each determination area.

In the above-described embodiment, the $\lambda_{415}$ image, the $\lambda_{460}$ image, the $\lambda_{540}$ image, the $\lambda_{600}$ image, and the $\lambda_{630}$ image are sequentially captured respectively by light beams in five wavelength bands with respective center wavelengths of 415 nm, 460 nm, 540 nm, 600 nm and 630 nm. However, at least two of these images may be captured simultaneously. For example, an image may be acquired using a Bayer-type image sensor provided with an RGB color filter. In this case, it is possible to obtain a series of images by emitting light beams with the center wavelengths of 415 nm, 540 nm and 600 nm at a first timing and emitting light beams with the center wavelengths of 460 nm and 630 nm at a subsequent second timing. The color filter is not limited to this, and for example, an image sensor provided with five types of color filters corresponding to the light source wavelengths may be used. In this case, images of all bands can be acquired simultaneously.

In the above-described embodiment, the overlapping of the blood vessels is determined based on whether the edge direction match or do not match. However, for example, a Sum of Absolute Difference (SAD) value may be obtained for each local area, as shape information about a subject in each image. Then, whether there is the overlap may be determined whether there is correlation between the shape information pieces. Specifically, the determination unit 112 determines that there is no overlap if the SAD is low, and determines that there is an overlap if the SAD is high. Furthermore, Sum of Squared Difference (SSD), normalized cross correlation (NCC), zero mean normalized cross correlation (ZNCC), or the like may be used. Alternatively, an eigenvector for each local region may be calculated as shape information for each wavelength using a Hessian matrix, and overlap determination may be performed using a difference in the resultant vectors. In this case, if the difference is small, it is determined that there is no overlap, and if the difference is large, it is determined that there is an overlap.

Figure 11:
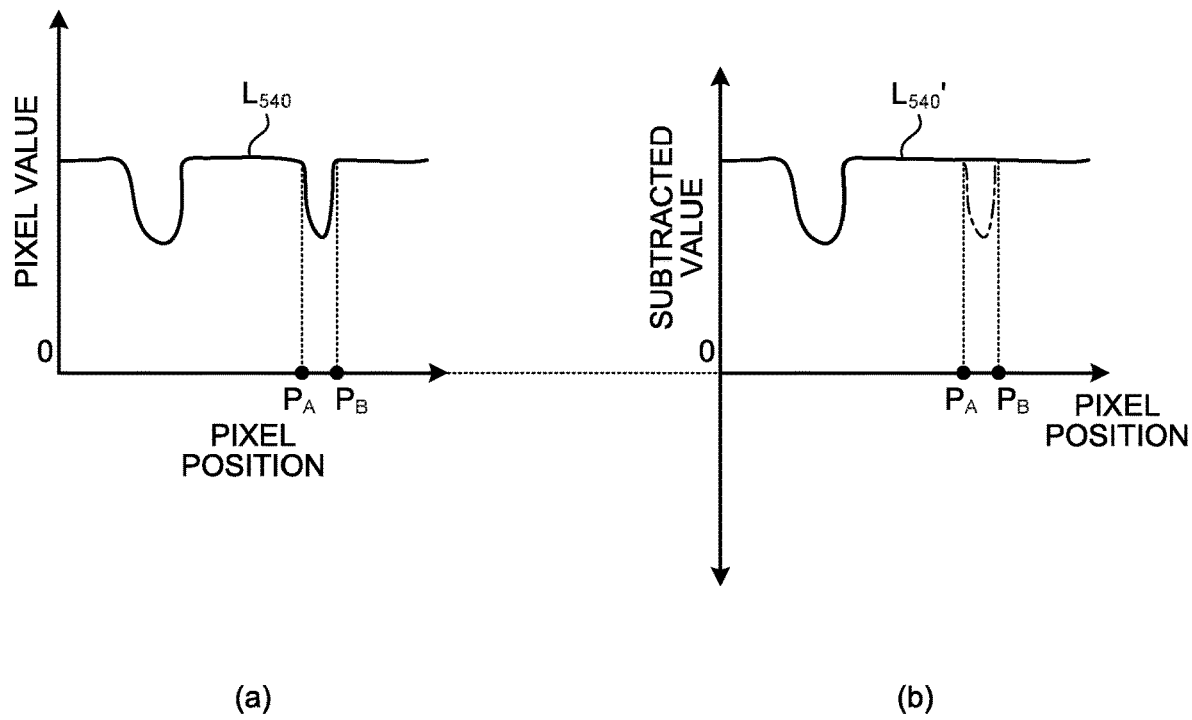
FIG. 11 is a diagram illustrating another example of processing of extracting light-absorption information about a deep layer according to an embodiment of the disclosure.

In addition to the processing of extracting light-absorption information according to the above-described embodiment, the light-absorption information may be extracted after interpolation of a value in the $\lambda_{540}$ image determined to involve overlap using a pixel with no overlap in the vicinity of the pixel. FIG. 11 is a diagram illustrating another example of processing of extracting light-absorption information about a deep layer according to an embodiment of the disclosure. A curve $L_{540}$ illustrated in (a) of FIG. 11 corresponds to the curve $L_{540}$ illustrated in (a) of FIG. 7. For example, in the case of the curve $L_{540}$ illustrated in (a) of FIG. 11, in an area from the pixel $P_A$ from the pixel $P_B$ determined to involve overlap, a 5×5 pixel area around a target pixel of the $\lambda_{540}$ image (here, an interpolation target pixel in the area from the pixel $P_A$ to the pixel $P_B$) is referred to, and the average value of the pixels determined to involve no overlapping in the area may be used as the interpolation value. For example, when extracting the light-absorption information of the $\lambda_{415}$ image, a curve $L_{540}'$ is obtained in which the pixel values at the positions where the middle layer blood vessel and the surface layer blood vessels overlap in the $\lambda_{540}$ image are replaced by pixel values with no overlap (see (b) of FIG. 11). In (b) of FIG. 11, a dashed-dotted line represents the curve $L_{540}$ illustrated in (a) of FIG. 11. On the curve $L_{540}'$, a part of the information about the middle layer blood vessel is lost, and therefore, when the $\lambda_{540}$ image is subtracted from the $\lambda_{415}$ image, the light-absorption information (negative value) of the surface layer blood vessel can be extracted.

Figure 12:
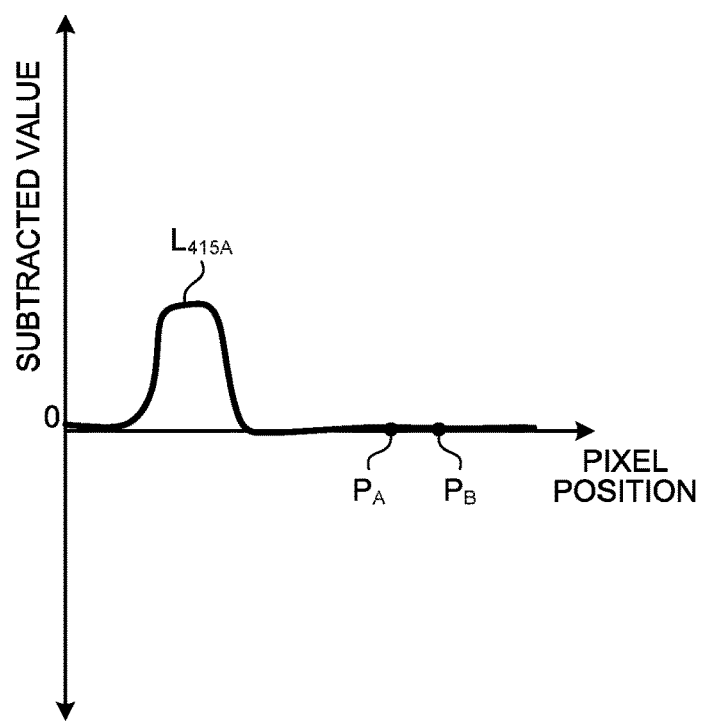
FIG. 12 is a diagram illustrating another example of processing of extracting light-absorption information about a deep layer according to an embodiment of the disclosure.

In addition, after light-absorption information is extracted using a conventional method, interpolation processing of light-absorption information of a portion determined to have overlap may be performed on the extraction result of the light-absorption information. FIG. 12 is a diagram illustrating another example of processing of extracting light-absorption information about a deep layer according to an embodiment of the disclosure. A curve $L_{415A}$ illustrated in FIG. 12 is obtained by subtracting the curve $L_{540}$ not multiplied by the coefficient from the curve $L_{415}$ illustrated in (a) of FIG. 7. In this extraction processing, first of all, light-absorption information is extracted by a conventional method. With the conventional extraction processing, the portion to be extracted (between the pixel $P_A$ and the pixel $P_B$ in FIG. 12) has a zero or positive value, and the image of the surface layer blood vessel is lost in the overlapping portion. After that, the light-absorption information (negative value) of the surface layer blood vessel is extracted by interpolating the extraction result of a pixel in the vicinity determined to have no overlap, for the pixel determined to have overlap of the blood vessels of different layers. In this case, in the calculation unit 100, the edge direction determination unit 111 determines the edge direction as described above, and the light-absorption information extraction unit 120 determines the extending direction of the blood vessel from the determination result of this edge direction. The interpolated light-absorption information is generated by performing interpolation processing using the pixel values of the pixels along the direction in which the blood vessel extends in the $\lambda_{415}$ image. For example, if the blood vessel extends along the horizontal line direction of the image, interpolation processing is executed using pixels along the horizontal line.

In the embodiment described above, although it has been described that light-absorption information about an arbitrary depth is extracted by subtraction processing between images. However, the disclosure is not limited to this, for example, light-absorption information may be extracted using a ratio between images. For example, when extracting the light-absorption information about the surface layer, the light-absorption information about the surface layer can be extracted by extracting a pixel in which the value of $\lambda_{415}$ image/($\alpha \times \lambda_{540}$ image) is smaller than 1.

In the above-described embodiment, the coefficient by which the $\lambda_{540}$ image is multiplied is described to be set based on the overlap determination result. However, the $\lambda_{415}$ image and the $\lambda_{600}$ image may be multiplied by the coefficient. In this case, the coefficient is set to 1 if there is no overlap, and the coefficient is set to a value smaller than 1 if there is an overlap. As described above, in the disclosure, a contribution ratio of the $\lambda_{540}$ image (second image) with the overlap may be made higher than the contribution ratio of the $\lambda_{415}$ image and the $\lambda_{600}$ image (first image).

In the above-described embodiment, the light-absorption information about the surface layer and the deep layer is extracted and the blood vessels of each layer are visualized. Alternatively, the blood vessels of any one of the layers may be visualized or the light-absorption information about the middle layer may be extracted according to an input from the user. When extracting a blood vessel of the middle layer, for example, the absorption information is extracted by subtracting the $\lambda_{415}$ image and the $\lambda_{600}$ image from the $\lambda_{540}$ image.

As described above, the image processing device, the operation method of the image processing device, and the operation program for the image processing device according to the disclosure is advantageous for visualizing a blood vessel at a certain depth in a case that blood vessels at different depths exist at the same position of the images.

The disclosure can achieve an effect that blood vessels at a specific depth can be visualized for a portion of images where blood vessels are at different depths.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
   an image acquiring unit configured to acquire a plurality of images that are captured with a same angle of view and are different from each other in a wavelength band of illumination light;
   a processor including hardware,
   wherein the processor is configured to
   determine, based on a first image and a second image different from the first image in the plurality of images, whether a first light absorber in a living body in the first image and a second light absorber in a living body in the second image overlap in a depth direction of a living body, and
   extract light-absorption information as a result of absorption by the first light absorber, by using the first image, the second image, and a determination result.

2. The image processing device according to claim 1, wherein
   when it is determined that the first absorber and the second light absorber overlap, the processor is configured to extract the light-absorption information with a contribution ratio of the second image with which the light-absorption information is extracted set to be relatively higher than a contribution ratio of the first image.

3. The image processing device according to claim 2, wherein
the processor is configured to extract the light-absorption information by subtracting a pixel value of the second image multiplied by a coefficient from a pixel value of the first image.

4. The image processing device according to claim 2, wherein
the processor is configured to extract the light-absorption information by dividing a pixel value of the first image by a pixel value of the second image multiplied by a coefficient.

5. The image processing device according to claim 1, wherein
when it is determined that the first absorber and the second light absorber overlap, the processor is configured to extract the light-absorption information about the first light absorber by interpolation processing.

6. The image processing device according to claim 5, wherein
when it is determined that the first absorber and the second light absorber overlap, the processor is configured to extract the light-absorption information about the first light absorber by interpolating a pixel value of a pixel of the second image by using a pixel value of a pixel determined to have no overlap among pixels around the pixel value of the pixel of the second image, and then by using the pixel value of the first image and the pixel value of the second image interpolated.

7. The image processing device according to claim 5, wherein
the processor is configured to
extract the light-absorption information as a result of absorption by the first light absorber by using the first image and the second image, and
extract, based on an extraction result that the light-absorption information is extracted and on a determination result that the first absorber and the second light absorber overlap, the light-absorption information about the first light absorber by interpolating light-absorption information corresponding to a pixel determined to have overlap by using a pixel value of a pixel determined to have no overlap among pixels around the pixel determined to have overlap.

8. The image processing device according to claim 7, wherein
the processor is configured to extract the light-absorption information about the first light absorber by interpolating light-absorption information corresponding to the pixel determined to have overlap by using the pixel value of the pixel determined to have no overlap of among pixels in a direction in which the first light absorber extends.

9. The image processing device according to claim 1, wherein
the processor is configured to determine whether the first absorber and the second light absorber overlap based on a correlation between shapes of the first image and the second image.

10. The image processing device according to claim 9, wherein
the processor is configured to generate shape information about subjects in the first image and the second image, and determine whether the first absorber and the second light absorber overlap based on the shape information.

11. The image processing device according to claim 9, wherein
the processor is configured to determine edge directions in the first image and the second image, and determine whether the first absorber and the second light absorber overlap based on a determination result of the edge directions.

12. The image processing device according to claim 11, wherein
the processor is configured to use a band pass filter to extract a frequency component preset, determine the edge directions in the first image and the second image after the frequency component has been extracted, and determine whether the first absorber and the second light absorbers overlap based on a determination result of the edge directions after the frequency component has been extracted.

13. The image processing device according to claim 9, wherein
the processor is configured to determine whether the first absorber and the second light absorber overlap based on a difference between the first image and the second image.

14. The image processing device according to claim 1 wherein
the processor is further configured to generate a display image by using at least one of the plurality of images and the light-absorption information.

15. An endoscope system comprising:
an endoscope configured to generate image data by imaging an inside of a body of a subject when being inserted into the subject; and
the image processing device according to claim 1, the image processing device being configured to execute image processing with respect to an endoscopic image corresponding to the image data generated by the endoscope.

16. An operation method of an image processing device, the operation method comprising:
acquiring a plurality of images that are captured with a same angle of view and are different from each other in a wavelength band of illumination light;
determining, based on a first image and a second image different from the first image in the plurality of images, whether a first light absorber in a living body in the first image and a second light absorber in a living body in the second image overlap in a depth direction of a living body in the images; and
extracting light-absorption information as a result of absorption by the first light absorber, by using the first image and the second image and a determination result obtained by the determining.

17. A non-transitory computer-readable recording medium with an executable program stored thereon, the program being an operation program of an image processing device and causing a computer to execute:
acquiring a plurality of images that are captured with a same angle of view and are different from each other in a wavelength band of illumination light;
determining, based on a first image and a second image different from the first image in the plurality of images, whether a first light absorber in a living body in the first image and a second light absorber in a living body in the second image overlap in a depth direction of a living body in the images; and extracting light-absorption information as a result of absorption by the first light absorber, by using the first image and the second image and a determination result obtained by the determining.

* * * * *